US007750156B2

(12) United States Patent
Kiyokawa et al.

(10) Patent No.: US 7,750,156 B2
(45) Date of Patent: Jul. 6, 2010

(54) METHOD OF PRODUCING AMINOPHENOL COMPOUNDS

(75) Inventors: Hiroshi Kiyokawa, Nara (JP); Shinji Aki, Itano (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 532 days.

(21) Appl. No.: 10/593,968

(22) PCT Filed: Mar. 25, 2005

(86) PCT No.: PCT/JP2005/006408

§ 371 (c)(1),
(2), (4) Date: Sep. 22, 2006

(87) PCT Pub. No.: WO2005/092832

PCT Pub. Date: Oct. 6, 2005

(65) Prior Publication Data

US 2007/0219374 A1 Sep. 20, 2007

(30) Foreign Application Priority Data

Mar. 25, 2004 (JP) .............................. 2004-089652

(51) Int. Cl.
C07D 241/04 (2006.01)
C07D 401/00 (2006.01)
C07D 211/40 (2006.01)

(52) U.S. Cl. ...................... 544/358; 546/189; 546/192; 546/216

(58) Field of Classification Search ................. 546/189, 546/192, 216; 544/358
See application file for complete search history.

(56) References Cited

U.S. PATENT DOCUMENTS 4,212,823 A   7/1980  Müller
5,202,488 A   4/1993  Jacobson

FOREIGN PATENT DOCUMENTS

| JP | 62-29557 | 2/1987 |
| SU | 189773 | 1/1967 |
| SU | 300461 | 6/1971 |
| WO | WO 02/083030 A2 | 10/2002 |

OTHER PUBLICATIONS

Haga et al.; "Condensations of 1,4-Cyclohexanediones and Secondary Aromatic Amines. II. N-Phenylation of Diarylamines:"; Bulletin of the Chemical Society of Japan; vol. 59, No. 3, pp. 803-807, (1986).
Leonard et al.; "Unsaturated Amines. IX. Through Bis-Enamines to Aromatics", Journal of Organic chemistry, vol. 21, -pp. 1187-1188, (1956).
Harris et al.; "Improved Functional Group Compatibility in the Palladium-Catalyzed Synthesis of Aryl Amines"; Organic Letters, vol. 4, No. 17, pp. 2885-2888, (2002).
Reiker et al; "NMR-Studien an Chinonanilen"; Terrahedron, vol. 23, pp. 3723-3732, (1967).
Figueras et al.; "The Synthesis and Spectral Properties of Some N-Substituted Derivatives of Phenol Blue"; J. Org. Chem. vol. 36, No. 23, pp. 3497-3501, (1971).
Haga et al.; "Condensations of 1,4-Cyclohexanediones and Secondary Aromatic Amines. The Formation of Alkyldiarylamines and Triarylamines"; Bulletin of the Chemical Society of Japan; vol. 57, No. 6, pp. 1586-1590, (1984).
Synthesis, 1982, No. 6, 471-472.
Lennon M., Proctor G.R., Journal of the Chemical Society, Perk. Trans. 1, 1979, 8, 2009-2012.

*Primary Examiner*—Taylor Victor Oh
(74) *Attorney, Agent, or Firm*—Finnegan, Henderson, Farabow, Garrett & Dunner, L.L.P.

(57) ABSTRACT

The present invention provides an industrially advantageous method of producing aminophenol compounds represented by the formula (1) by a simple and easy procedure at a high yield and a high purity. The present invention provides a method of producing an aminophenol compound represented by the formula (1): (wherein each of $R^1$ and $R^2$, which may be the same or different, is a hydrogen atom, a substituted or unsubstituted lower alkyl group or the like; $R^1$ and $R^2$, taken together with the adjacent nitrogen atom, may form a 5- or 6-membered heterocycle with or without other intervening heteroatoms; the heterocycle may be substituted by 1 to 3 substituents selected from the group consisting of a hydroxyl group, a substituted or unsubstituted lower alkyl group, a substituted or unsubstituted aryl group, a substituted or unsubstituted aryloxy group and the like; and the hydroxyl group in the formula (1) is substituted on the 2- or 4-position to the amino group on the phenyl ring), which comprises allowing a cyclohexanedione compound represented by the formula (2) to react with an amine compound represented by the formula (3) (wherein $R^1$ and $R^2$ are as defined above), under a neutral or basic condition.

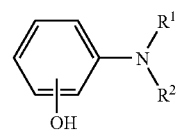

(1)

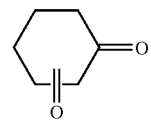

(2)

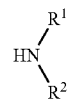

(3)

9 Claims, No Drawings

METHOD OF PRODUCING AMINOPHENOL COMPOUNDS

TECHNICAL FIELD

The present invention relates to a method of producing aminophenol compounds.

BACKGROUND ART

Aminophenol compounds represented by the formula (1) and salts thereof:

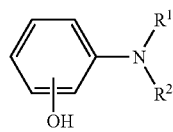
(1)

(wherein each of $R^1$ and $R^2$, which may be the same or different, is a hydrogen atom, a substituted or unsubstituted lower alkyl group, a substituted or unsubstituted aryl group or a substituted or unsubstituted heterocyclic group; $R^1$ and $R^2$, taken together with the adjacent nitrogen atom, may form a 5- or 6-membered heterocycle with or without other intervening heteroatoms; the heterocycle may be substituted by 1 to 3 substituents selected from the group consisting of a hydroxyl group, a substituted or unsubstituted lower alkyl group, a substituted or unsubstituted aryl group, a substituted or unsubstituted aryloxy group, a substituted or unsubstituted heterocyclic group and a substituted or unsubstituted heterocyclic group-substituted oxy group; and the hydroxyl group in the formula (1) is substituted on the second or the fourth position of the phenyl ring) are useful as a synthesized intermediate for various pharmaceutical agents (preferably antitubercular agents) and agrichemicals.

Heretofore, as a method of producing aminophenol compounds, for example, methods shown in the following Reaction scheme-1 and Reaction scheme-2 are known (Stephen L. Buchwald et al., Organic Letters, vol. 4, 2885 (2002)).

Reaction scheme-1

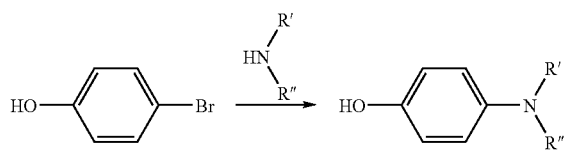

Reaction scheme-2

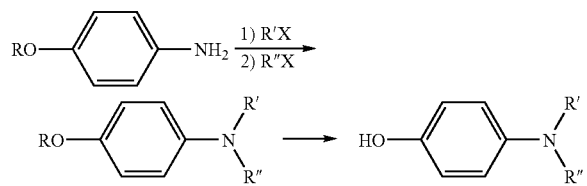

In the above-mentioned schemes, the group —NR'R" is a dibutyl amino group, a N-methylanilino group, a morpholino group, a 4-methylpiperidinyl group, a 4-hydroxypiperidinyl group, a 4-methylanilino group, a 4-methoxyanilino group and a 3,4-dimethoxyanilino group, and R is a protecting group of a hydroxyl group.

These methods, however, have various defects and therefore not suitable for an industrial production method.

For example, the method shown in the Reaction scheme-1 requires expensive basic or metal catalysts such as a palladium catalyst, aromatic triflate and a copper catalyst. The method shown in the Reaction scheme-2 requires a complicated step of protecting the hydroxyl group of phenol and then removing the protecting group.

Kazuo Haga et al. (Bull. Chem. Soc. Jpn., 57, 1586 (1984) and Bull. Chem. Soc. Jpn., 59, 803-807 (1986)) disclose that the reaction of 1,4-cyclohexanedione and a secondary amine in the presence of an acid catalyst does not afford an aminophenol compound or if do, the yield is only 4 to 12%, and the main product of the reaction is an aniline compound.

A. Reiker et al. (Tetrahedron, 23, 3723 (1967)), J. Figueras et al. (J. Org. Chem., 36, 3497 (1971)) and JP-A-62-29557 disclose that the reaction of 1,4-benzoquinone and a primary amine in the presence of an acid catalyst affords a quinone monoimine compound, and the generated quinone monoimine compound must be further reduced in order to produce the objective aminophenol compound.

DISCLOSURE OF THE INVENTION

An object of the present invention is to provide an industrially advantageous method of producing aminophenol compounds represented by the formula (1) by simple and easy procedures at a high yield and high purity.

To solve the above-mentioned problems, the present inventors have conducted intensive studies on the method of producing aminophenol compounds represented by the formula (1) and as a result, have found that the above-mentioned problems can be solved by allowing a cyclohexanedione compound of the formula (2) to react with an amine compound of the formula (3) under a neutral or basic condition. The present invention has been completed based on these findings.

The present invention provides a method of producing an aminophenol compound represented by the formula (1)

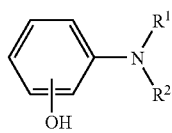
(1)

(wherein each of $R^1$ and $R^2$, which may be the same or different, is a hydrogen atom, a substituted or unsubstituted lower alkyl group, a substituted or unsubstituted aryl group or a substituted or unsubstituted heterocyclic group; $R^1$ and $R^2$, taken together with the adjacent nitrogen atom, may form a 5- or 6-membered heterocycle with or without other intervening heteroatoms; the heterocycle may be substituted by 1 to 3 substituents selected from the group consisting of a hydroxyl group, a substituted or unsubstituted lower alkyl group, a substituted or unsubstituted aryl group, a substituted or unsubstituted aryloxy group, a substituted or unsubstituted heterocyclic group and a substituted or unsubstituted heterocyclic group-substituted oxy group; and the hydroxyl group in the formula (1) is substituted on the 2- or 4-position to the amino group on the phenyl ring), which comprises allowing a cyclohexanedione compound represented by the formula (2)

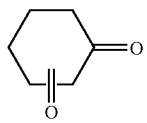
(2)

to react with an amine compound represented by the formula (3)

(3)

(wherein $R^1$ and $R^2$ are as defined above), under a neutral or basic condition.

The present invention also provides a method according to the above-mentioned method, wherein each of $R^1$ and $R^2$, which may be the same or different, is a hydrogen atom; a lower alkyl group which may have 1 to 3 substituents selected from the group consisting of a halogen atom, a hydroxyl group, a substituted or unsubstituted aryl group and a substituted or unsubstituted heterocyclic group; an aryl group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; or a heterocyclic group which may have 1 to 3 substituents selected from the group consisting of a lower alkyl group which nay have 1 to 3 substituents selected from the group consisting of a halogen atom and a hydroxyl group, a lower alkoxy groups which may have 1 to 3 substituents selected from the group consisting of a halogen atom and a hydroxyl group, and halogen atoms;

$R^1$ and $R^2$, taken together with the adjacent nitrogen atom, may form a 5- or 6-membered heterocycle with or without other intervening heteroatoms; and the heterocycle may be substituted by 1 to 3 substituents selected from the group consisting of a hydroxyl group; a lower alkyl group which may have 1 to 3 substituents selected from the group consisting of a halogen atom, a hydroxyl group, a substituted or unsubstituted aryl group and a substituted or unsubstituted heterocyclic group; an aryl group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; an aryloxy group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; a heterocyclic group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; and a heterocyclic group-substituted oxy group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms.

The present invention provides a method according to the above-mentioned method, wherein each of $R^1$ and $R^2$, which may be the same or different, is a hydrogen atom; a lower alkyl group which may have 1 to 3 substituents selected from the group consisting of a halogen atom, a hydroxyl group, a substituted or unsubstituted aryl group and a substituted or unsubstituted heterocyclic group; an aryl group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; or a heterocyclic group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms.

The present invention provides a method according to the above-mentioned method, wherein $R^1$ and $R^2$, taken together with the adjacent nitrogen atom, may form a 5- or 6-membered heterocycle with or without other intervening heteroatoms, and the heterocycle may be substituted by 1 to 3 substituents selected from the group consisting of a hydroxyl group; a lower alkyl group which may have 1 to 3 substituents selected from the group consisting of a halogen atom, a hydroxyl group, a substituted or unsubstituted aryl group and a substituted or unsubstituted heterocyclic group; an aryl group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; an aryloxy group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; a heterocyclic group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; and a heterocyclic group-substituted oxy group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms.

The present invention provides a method according to the above-mentioned methods, wherein the aryl group is a phenyl group or a naphthyl group; the aryloxy group is a phenoxy group or a naphthyloxy group; the heterocyclic group is a 5- or 6-membered saturated or unsaturated heterocyclic group; and the heterocyclic group-substituted oxy group is an oxy group substituted by a 5- or 6-membered saturated or unsaturated heterocyclic group.

The present invention provides a method according to the above-mentioned method, wherein the aminophenol compound is 1-(4-hydroxyphenyl)-4-(4-trifluoromethoxyphenoxy)piperidine, 1-(4-hydroxyphenyl)-4-hydroxypiperidine, 1-(4-hydroxyphenyl)piperidine, 1-(4-hydroxyphenyl)-4-methylpiperazine, N-(4-hydroxyphenyl)-N-methylaniline, N-(4-hydroxyphenyl)aniline or N-(4-hydroxyphenyl)dibenzylamine.

The present invention provides a method according to the above-mentioned methods, which is conducted in the presence of a dehydrogenating agent, wherein the dehydrogenating agent is used in an amount of at least 1% by weight based on an amount of the amine compound of the formula (3).

The present invention provides a method according to the above-mentioned methods, which is conducted without a dehydrogenating agent.

The present invention provides a method according to the above-mentioned methods, which is conducted under a neutral condition.

The present invention provides a method according to the above-mentioned methods, which is conducted in the presence of a basic compound, wherein the basic compound is used in an amount of 0.5 to 5 mole based on 1 mole of the amine compound of the formula (3).

The present invention provides a method according to the above-mentioned methods, wherein a reaction is conducted at a reaction temperature of room temperature to 150° C.

The present invention provides a method according to the above-mentioned methods, wherein the cyclohexanedione compound of the formula (2) is used in an amount of equimolar amount to 10 mole based on 1 mole of the amine compound of the formula (3).

The groups described in the formula (1) are more specifically as follows.

Examples of substituted or unsubstituted lower alkyl group include linear or branched alkyl groups having 1 to 6 carbon atoms, which may have 1 to 3 substituents selected from the group consisting of a halogen atom, a hydroxyl group, a substituted or unsubstituted aryl group and a substituted or unsubstituted heterocyclic group, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl, benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, α-naphthylmethyl, β-naphthylmethyl, 2-(α-naphthyl)ethyl, 1-(β-naphthyl)ethyl, 3-(α-naphthyl)propyl, 4-(β-naphtyl)butyl, 5-α-naphthyl)pentyl, 6-(β-naphthyl)hexyl, 1,1-dimethyl-2-α-naphthyl)ethyl, 2-methyl-3-(β-naphthyl)propyl, 3-furylmethyl, (4-morpholino)methyl, (1-piperazinyl)methyl, (1-pyrrolidinyl)methyl, (1-piperidinyl)methyl, (3-pyridyl)methyl, 2-(2-thienyl)ethyl, 1-(3-pyrrolyl)ethyl, 3-(2-oxazolyl)propyl, 4-(2-thiazolyl)butyl, 5-(2-imidazolyl)pentyl, 6-(2-pyridyl)hexyl, 1,1-dimethyl-2-(2-pyrimidyl)ethyl and 2-methyl-3-(3-pyridazyl)propyl.

Examples of the substituted or unsubstituted aryl group include phenyl groups which may have 1 to 3 substituents and naphthyl groups which may have 1 to 3 substituents. Examples of the substituent of the aryl group include linear or branched alkyl groups having 1 to 6 carbon atoms, which may have 1 to 3 substituents selected from the group consisting of a halogen atom and a hydroxyl group, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl and the like; linear or branched alkoxy groups having 1 to 6 carbon atoms, which may have 1 to 3 substituents selected from the group consisting of a halogen atom and a hydroxyl group, such as methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy and the like; or halogen atoms such as fluorine atom, bromine atom, chlorine atom and iodine atom. When two or more substituents are present, these substituents may be the same or different.

Examples of the substituted or unsubstituted heterocyclic group include heterocyclic groups which may have 1 to 3 substituents. Examples of the heterocyclic group include 5- or 6-membered saturated or unsaturated heterocyclic groups such as furyl, thienyl, pyrrolyl, 2H-pyrrolyl, oxazolyl, isooxazolyl, thiazolyl, isothiazolyl, imidazolyl, pirazolyl, furazanyl, pyranyl, pyridyl, pyridazyl, pyrimidyl, pyrazyl, piperidyl, piperazyl, pyrrolidinyl, morpholino and the like. Examples of the substituent on the heterocyclic group include linear or branched alkyl groups having 1 to 6 carbon atoms, which may have 1 to 3 substituents selected from the group consisting of a halogen atom and a hydroxyl group, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl and the like; linear or branched alkoxy groups having 1 to 6 carbon atoms, which may have 1 to 3 substituents selected from the group consisting of a halogen atom and a hydroxyl group, such as methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy and the like; or halogen atoms such as fluorine atom, bromine atom, chlorine atom and iodine atom. When two or more substituents are present, these substituents may be the same or different.

Examples of the substituted or unsubstituted aryloxy group include phenoxy groups which may have 1 to 3 substituents and naphthyloxy groups which may have 1 to 3 substituents. Examples of the substituent of the aryl group include linear or branched alkyl groups having 1 to 6 carbon atoms, which may have 1 to 3 substituents selected from the group consisting of a halogen atom and a hydroxyl group, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl and the like; linear or branched alkoxy groups having 1 to 6 carbon atoms, which may have 1 to 3 substituents selected from the group consisting of a halogen atom and a hydroxyl group such as methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy and the like; or halogen atoms such as fluorine atom, bromine atom, chlorine atom and iodine atom. When two or more substituents are present, these substituents may be the same or different.

The substituted or unsubstituted heterocyclic group-substituted oxy group means, for example, heterocyclic group-substituted oxy groups which may have 1 to 3 substituents. Examples of the heterocyclic group-substituted oxy group include oxy groups substituted by a 5- or 6-membered saturated or unsaturated heterocyclic group, such as furyloxy, thienyloxy, pyrrolyloxy, 2H-pyrrolyloxy, oxazolyloxy, isooxazolyloxy, thiazolyloxy, isothiazolyloxy, imidazolyloxy, pirazolyloxy, furazanyloxy, pyranyloxy, pyridyloxy, pyridazyloxy, pyrimidyloxy, pyrazyloxy, piperidyloxy, piperazyloxy, pyrrolidinyloxy, morpholinooxy and the like. Examples of the substituent of the heterocyclic group include linear or branched alkyl groups having 1 to 6 carbon atoms, which may have 1 to 3 substituents selected from the group consisting of a halogen atom and a hydroxyl group, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl and the like; linear or branched alkoxy groups having 1 to 6 carbon atoms, which may have 1 to 3 substituents selected from the group consisting of a halogen atom and a hydroxyl group, such as methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy and the like; or halogen atoms such as fluorine atom, bromine atom, chlorine atom and iodine atom. When two or more substituents are present, these substituents may be the same or different.

Examples of the 5- or 6-membered heterocyclic group formed by $R^1$ and $R^2$ taken together with an adjacent nitrogen atom with or without other intervening heteroatoms include pyrrolidinyl, piperidinyl, piperazinyl, morpholino and thiomorpholino groups. The heterocyclic group may be substituted by 1 to 3 substituents selected from the group consisting of a hydroxyl group, the above-mentioned substituted or unsubstituted lower alkyl group, the above-mentioned substituted or unsubstituted aryl group, the above-mentioned substituted or unsubstituted aryloxy group, the above-mentioned substituted or unsubstituted heterocyclic group and the above-mentioned substituted or unsubstituted heterocyclic group-substituted oxy group. When two or more substituents are present, these substituents may be the same or different.

The method of producing an aminophenol compound of the formula (1) of the present invention is described below.

The aminophenol compound of the formula (1) according to the present invention is produced by allowing a cyclohexanedione compound represented by the formula (2) to react with an amine compound represented by the formula (3) under a neutral or basic condition.

The reaction of the cyclohexanedione compound represented by the formula (2) and the amine compound represented by the formula (3) are conducted in an appropriate solvent in the presence or absence of a dehydrogenating agent with or without a basic compound.

Examples of the solvent to be used include halogenated hydrocarbons such as dichloromethane, chloroform and carbon tetrachloride, lower alcohols such as methanol, ethanol and isopropanol, ketones such as acetone and methyl ethyl ketone, ethers such as diethylether, dioxane, tetrahydrofuran, ethylene glycol monomethyl ether and ethylene glycol dimethyl ether, aromatic hydrocarbons such as benzene, toluene and xylene, esters such as ethyl acetate and methyl acetate, acetonitrile, pyridine, 2,4,6-collidine, dimethylsulfoxide, dimethylformamide, hexamethylphosphoric triamide and a mixed solvent of these.

Examples of the dehydrogenating agent include metal catalysts such as palladium, platinum, iridium, rhodium, manganese, ruthenium and nickel. The metal catalyst may be one in which the above-mentioned metal is held by an inert carrier such as activated carbon, alumina, barium sulfate and calcium carbonate, as in palladium-carbon.

The dehydrogenating agent is used alone or in a mixture of two or more kinds.

The amount of the dehydrogenating agent is usually at least 1% by weight, preferably about 1 to 200% by weight based on an amount of the amine compound of the formula (3).

As the basic compound, a wide variety of known organic bases and inorganic bases can be used.

Examples of the organic base include triethyl amine, trimethyl amine, pyridine, dimethylaniline, N-ethyldiisopropylamine, dimethylaminopyridine, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and 1,8-bis(dimethylamino)naphthalene.

Examples of the inorganic base include carbonates such as sodium carbonate, potassium carbonate, cesium carbonate, sodium hydrogen carbonate and potassium hydrogen carbonate; metal hydroxides such as sodium hydroxide, potassium hydroxide, calcium hydroxide and cesium hydroxide; phosphates such as tripotassium phosphate, dipotassium hydrogen phosphate, trisodium phosphate and disodium hydrogen phosphate; potassium hydride, sodium hydride, potassium, sodium and sodium amides.

The basic compound is used alone or in a mixture of two or more kinds.

The amount of the basic compound is usually 0.5 to 5 mole, preferably 0.5 to 2 mole based on 1 mole of the amine compound of the formula (3).

The amount of the cyclohexanedione compound of the formula (2) is usually equimolar to about 10 mole, preferably equimolar to about 2 mole based on 1 mole of the amine compound of the formula (3).

The reaction favorably proceeds usually at about room temperature to about 150° C., preferably at about room temperature to about 100° C. The reaction is generally completed in about 1 to 15 hours.

The reaction can be conducted in the presence or absence of a dehydrogenating agent, but the reaction proceeds even by an open system (with air being contacted) or by bubbling air or oxygen in the system.

The cyclohexanedione compound represented by the formula (2) which is used as a starting material is a readily available, known compound.

Some of the amine compounds of the formula (3) are novel compounds and can be produced, for example, by the method of the following Reaction scheme-3.

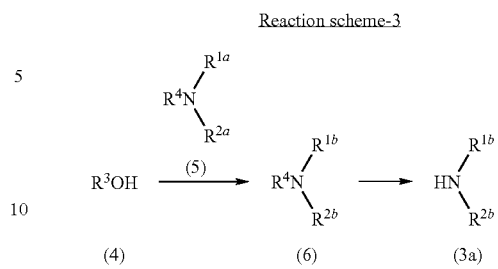

Reaction scheme-3

In the formulas, $R^3$ is a substituted or unsubstituted aryl group; $R^{1a}$ and $R^{2a}$, taken together with the adjacent nitrogen atom, form a 5- or 6-membered heterocycle with or without other intervening heteroatoms (in which the heterocycle is substituted by at least one group X, and may be further substituted by 1 to 2 substituents selected from the group consisting of a hydroxyl group, a substituted or unsubstituted lower alkyl group, a substituted or unsubstituted aryl group, a substituted or unsubstituted aryloxy group, a substituted or unsubstituted heterocyclic group and a substituted or unsubstituted heterocyclic group-substituted oxy group); $R^{1b}$ and $R^{2b}$, taken together with the adjacent nitrogen atom, form a 5- or 6-membered heterocycle with or without other intervening heteroatoms (in which the heterocycle is substituted by at least one group $—OR^3$, and may be further substituted by 1 to 2 substituents selected from the group consisting of a hydroxyl group, a substituted or unsubstituted lower alkyl group, a substituted or unsubstituted aryl group, a substituted or unsubstituted aryloxy group, a substituted or unsubstituted heterocyclic group and a substituted or unsubstituted heterocyclic group-substituted oxy group); $R^4$ is a protecting group of an amino group; and X is a lower alkylsulfonyloxy group, a phenylsulfonyloxy group of which the phenyl ring may be substituted by a lower alkyl group or a halogen atom.

Examples of the protecting group of an amino group include a lower alkoxycarbonyl group, aryloxycarbonyl group and an aryl-substituted lower alkyl group.

Examples of the lower alkoxycarbonyl group include linear or branched alkoxycarbonyl groups having 1 to 6 carbon atoms, such as methoxycarbonyl, ethoxycarbonyl, propoxycarbonyl, butoxycarbonyl, tert-butoxycarbonyl, pentyloxycarbonyl and hexyloxycarbonyl groups.

Examples of the aryloxycarbonyl group include phenoxycarbonyl groups which may have 1 to 3 substituents and naphthyloxycarbonyl groups which may have 1 to 3 substituents. Examples of the substituent of the aryl group include linear or branched alkyl groups having 1 to 6 carbon atoms, which may have 1 to 3 substituents selected from the group consisting of a halogen atom and a hydroxyl group, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl and the like; linear or branched alkoxy groups having 1 to 6 carbon atoms, which may have 1 to 3 substituents selected from the group consisting of a halogen atom and a hydroxyl group, such as methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy and the like; or halogen atoms such as fluorine atom, bromine atom, chlorine atom and iodine atom. When two or more substituents are present, these substituents may be the same or different.

Examples of the aryl-substituted lower alkyl group include phenyl-substituted linear or branched alkyl groups having 1 to 6 carbon atoms, which may have 1 to 3 substituents and naphthyl-substituted linear or branched alkyl groups having 1 to 6 carbon atoms, which may have 1 to 3 substituents, such as benzyl, 2-phenylethyl, 1-phenylethyl, 3-phenylpropyl, 4-phenylbutyl, 5-phenylpentyl, 6-phenylhexyl, 1,1-dimethyl-2-phenylethyl, 2-methyl-3-phenylpropyl, α-naphthylmethyl, β-naphthylmethyl, 2-α-naphthyl)ethyl, 1-(β-naphthyl)ethyl, 3-(α-naphthyl)propyl, 4-(β-naphtyl)butyl, 5-α-naphthyl)pentyl, 6-(β-naphthyl)hexyl, 1,1-dimethyl-2-(α-naphthyl)ethyl and 2-methyl-3-(β-naphthyl)propyl. Examples of the substituent of the aryl group include linear or branched alkyl groups having 1 to 6 carbon atoms, which may have 1 to 3 substituents selected from the group consisting of a halogen atom and a hydroxyl group, such as methyl, ethyl, propyl, n-butyl, sec-butyl, tert-butyl, n-pentyl, n-hexyl, hydroxymethyl, 2-hydroxyethyl, 1-hydroxyethyl, 3-hydroxypropyl, 2,3-dihydroxypropyl, 4-hydroxybutyl, 1,1-dimethyl-2-hydroxyethyl, 5,5,4-trihydroxypentyl, 5-hydroxypentyl, 6-hydroxyhexyl, 1-hydroxyisopropyl, 2-methyl-3-hydroxypropyl, trifluoromethyl, trichloromethyl, chloromethyl, bromomethyl, fluoromethyl, iodomethyl, difluoromethyl, dibromomethyl, 2-chloroethyl, 2,2,2-trifluoroethyl, 2,2,2-trichloroethyl, 3-chloropropyl, 2,3-dichloropropyl, 4,4,4-trichlorobutyl, 4-fluorobutyl, 5-chloropentyl, 3-chloro-2-methylpropyl, 5-bromohexyl, 5,6-dichlorohexyl, 3-hydroxy-2-chloropropyl and the like; linear or branched alkoxy groups having 1 to 6 carbon atoms, which may have 1 to 3 substituents selected from the group consisting of a halogen atom and a hydroxyl group, such as methoxy, ethoxy, propoxy, n-butoxy, sec-butoxy, tert-butoxy, n-pentyloxy, n-hexyloxy, hydroxymethoxy, 2-hydroxyethoxy, 1-hydroxyethoxy, 3-hydroxypropoxy, 2,3-dihydroxypropoxy, 4-hydroxybutoxy, 1,1-dimethyl-2-hydroxyethoxy, 5,5,4-trihydroxypentyloxy, 5-hydroxypentyloxy, 6-hydroxyhexyloxy, 1-hydroxyisopropoxy, 2-methyl-3-hydroxypropoxy, trifluoromethoxy, trichloromethoxy, chloromethoxy, bromomethoxy, fluoromethoxy, iodomethoxy, difluoromethoxy, dibromomethoxy, 2-chloroethoxy, 2,2,2-trifluoroethoxy, 2,2,2-trichloroethoxy, 3-chloropropoxy, 2,3-dichloropropoxy, 4,4,4-trichlorobutoxy, 4-fluorobutoxy, 5-chloropentyloxy, 3-chloro-2-methylpropoxy, 5-bromohexyloxy, 5,6-dichlorohexyloxy, 3-hydroxy-2-chloropropoxy and the like; or halogen atoms such as fluorine atom, bromine atom, chlorine atom and iodine atom. When two or more substituents are present, these substituents may be the same or different.

The lower alkylsulfonyloxy group is constituted by an alkyl group having 1 to 6 carbon atoms and a sulfonyloxy group, and examples thereof include methanesulfonyloxy group, ethanesulfonyloxy group, propanesulfonyloxy group, butanesulfonyloxy group, pentanesulfonyloxy group and hexanesulfonyloxy group.

Examples of the phenylsulfonyloxy group of which the phenyl ring may be substituted by lower alkyl groups include benzenesulfonyloxy groups which may be substituted by 1 to 3 linear or branched alkyl groups having 1 to 6 carbon atoms, such as benzenesulfonyloxy group, o-toluenesulfonyloxy group, m-toluenesulfonyloxy group, p-toluenesulfonyloxy group, 2-ethylbenzenesulfonyloxy group, 3-ethylbenzenesulfonyloxy group, 4-ethylbenzenesulfonyloxy group, 2-propylbenzenesulfonyloxy group, 3-propylbenzenesulfonyloxy group, 4-propylbenzenesulfonyloxy group, 2,3-dimethylbenzenesulfonyloxy group, 2,4-dimethylbenzenesulfonyloxy group and 2,4,6-trimethylbenzenesulfonyloxy group.

The reaction of the compound of the formula (4) and the compound of the formula (5) are generally carried out in an appropriate inert solvent in the presence of a phase-transfer catalyst with or without a basic compound.

Examples of the inert solvent to be used include water, aromatic hydrocarbons such as benzene, toluene and xylene; ethers such as diethylether, tetrahydrofuran, dioxane, monoglyme and diglyme; halogenated hydrocarbons such as dichloromethane, dichloroethane, chloroform and carbon tetrachloride; lower alcohols such as methanol, ethanol, isopropanol, butanol, tert-butanol and ethyleneglycol; esters such as ethyl acetatd and methyl acetate; ketones such as acetone and methyl ethyl ketone; pyridines such as pyridine and 2,6-lutidine; acetonitrile; amides such as N,N-dimethylformamide, N,N-dimethylacetoamide and N-methylpyrrolidone; dimethylsulfoxide, hexamethylphosphoric triamide and a mixed solvent of these.

Examples of the phase-transfer catalyst include quaternary ammonium salts, phosphonium salts and pyridinium salts.

Examples of the quaternary ammonium salt include quaternary ammonium salts substituted by a group selected from the group consisting of a linear or branched alkyl group having 1 to 18 carbon atoms, a phenyl-substituted liner or branched alkyl group having 1 to 6 carbon atoms and a phenyl group, such as tetrabutyl ammonium chloride, tetrabutyl ammonium bromide, tetrabutyl ammonium fluoride, tetrabutyl ammonium iodide, tetrabutyl ammonium hydroxide, tetrabutyl ammonium bisulfite, tributylmethyl ammonium chloride, tributylbenzyl ammonium chloride, tetrapentyl ammonium chloride, tetrapentyl ammonium bromide, tetrahexyl ammonium chloride, benzyldimethyloctyl ammonium chloride, methyltrihexyl ammonium chloride, benzyldimethyloctadecanyl ammonium chloride, methyltridecanyl ammonium chloride, benzyltripropyl ammonium chloride, benzyltriethyl ammonium chloride, phenyltriethyl ammonium chloride, tetraethyl ammonium chloride and tetramethyl ammonium chloride.

Examples of the phosphonium salt include phosphonium salts substituted by a linear or branched alkyl group having 1 to 18 carbon atoms or a substituted amino group, such as tetrabutyl phosphonium chloride and tetrakis(tris(dimethylamino)phosphoranylideneamino)phosphonium chloride.

Examples of the pyridinium salt include pyridinium salts substituted by a linear or branched alkyl group having 1 to 18 carbon atoms, such as 1-dodecanyl pyridinium chloride.

The phase-transfer catalyst is used alone or in a mixture of two or more kinds.

The amount of the phase-transfer catalyst is usually 0.1 to 1 mole, preferably 0.1 to 0.5 mole based on 1 mole of the compound (4).

As the basic compound, a wide variety of known organic bases and inorganic bases can be used.

Examples of the organic base include metal alcoholates such as sodium methylate, sodium ethylate and sodium n-butoxide, pyridine, imidazole, N-ethyldiisopropylamine, dimethylaminopyridine, triethyl amine, trimethyl amine, dimethylaniline, N-methylmorpholine, 1,5-diazabicyclo[4.3.0]nonene-5 (DBN), 1,8-diazabicyclo[5.4.0]undecene-7 (DBU), 1,4-diazabicyclo[2.2.2]octane (DABCO) and 1,8-bis(dimethylamino)naphthalene.

Examples of the inorganic base include carbonates such as sodium carbonate, potassium carbonate, sodium hydrogen carbonate, potassium hydrogen carbonate and cesium carbonate; hydroxides such as sodium hydroxide, potassium hydroxide, cesium hydroxide and calcium hydroxide; hydrides such as sodium hydride and potassium hydride; phosphates such as tripotassium phosphate, dipotassium hydrogen phosphate, trisodium phosphate and disodium hydrogen phosphate; and alkali metals such as potassium and sodium. The inorganic base also includes sodium amides.

The basic compound is used alone or in a mixture of two or more kinds.

The amount of the basic compound is usually at least equimolar, preferably equimolar to 5 mole based on 1 mole of the compound (4).

The amount of the compound (5) is usually at least equimolar, preferably equimolar to 3 mole based on 1 mole of the compound (4).

The reaction of the compound of the formula (4) and the compound of the formula (5) favorably proceeds usually at about 0° C. to about 200° C., preferably at about 0° C. to about 150° C. The reaction is generally completed in about 5 minutes to 10 hours.

The reaction of obtaining a compound (3a) from a compound (6) is conducted in an appropriate solvent or without a solvent in the presence of an acid or a basic compound.

Examples of the solvent to be used include water, lower alcohols such as methanol, ethanol, isopropanol and tert-butanol, ketones such as acetone and methyl ethyl ketone, ethers such as diethylether, dioxane, tetrahydrofuran, monoglyme and diglyme, aliphatic acids such as acetic acid and formic acid, esters such as methyl acetate and ethyl acetate, halogenated hydrocarbons such as chloroform, dichloromethane, dichloroethane and carbon tetrachloride, amides such as N,N-dimethylformamide, N,N-dimethylacetoamide and N-methylpyrrolidone, dimethylsulfoxide, hexamethylphosphoric triamide and a mixed solvent of these.

Examples of the acid include mineral acids such as hydrochloric acid, sulfuric acid and hydrobromic acid, and organic acids such as formic acid, acetic acid, trifluoroacetic acid and sulfonic acids such as p-toluenesulfonic acid. Examples of the basic compound include carbonates such as sodium carbonate, potassium carbonate, cesium carbonate, sodium hydrogen carbonate and potassium hydrogen carbonate and metal hydroxides such as sodium hydroxide, potassium hydroxide, calcium hydroxide, cesium hydroxide and lithium hydroxide.

The amounts of the acid and the basic compound are usually at least 1 mole, preferably 1 to 10 mole, based on 1 mole of the compound (6).

The reaction favorably proceeds usually at about 0° C. to about 200° C., preferably at about 0° C. to about 150° C., and is generally completed in about 10 minutes to 30 hours.

When $R^4$ is an aryl-substituted lower alkyl group, the compound (3a) can also be obtained by reducing the compound (6).

The reduction reaction can be conducted, for example, by catalytic hydrogenation in the presence of a catalyst in an appropriate solvent. Examples of the solvent to be used include water, acetic acid, alcohols such as methanol, ethanol and isopropanol, hydrocarbons such as n-hexane and cyclohexane, ethers such as dioxane, tetrahydrofuran, diethylether and ethylene glycol dimethyl ether, esters such as ethyl acetate and methyl acetate, aprotic polar solvents such as dimethylformamide and a mixed solvent of these. Examples of the catalyst to be used include palladium, palladium-black, palladium-carbon, platinum, platinum oxide, copper chromite, Raney nickel and a mixture of these. The amount of the catalyst is usually about 0.02 to 1-fold by weight based on an amount of the compound (6). The reaction temperature is usually about −20° C. to about 100° C., preferably about 0° C. to about 80° C. and the hydrogen pressure is usually 1 to 10 atm. The reaction is generally completed in about 0.5 to 20 hours.

A 2,3-dihydro-6-nitroimidazo[2,1-b]oxazole compound represented by the formula (9) which is useful as an antitubercular agents can be obtained from the aminophenol compound of the formula (1) according to the present invention by the method described in the following Reaction scheme-4.

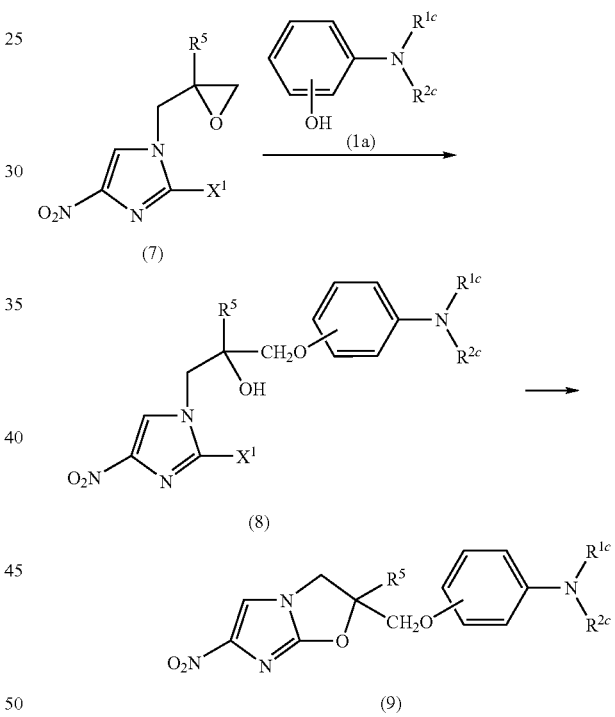

Reaction scheme-4

In the formulas, $X^1$ is a halogen atom or a nitro group; $R^5$ is a hydrogen atom or a C1-6 alkyl group; each of $R^{1c}$ and $R^{2c}$, which may be the same or different, is a hydrogen atom, a lower alkyl group, a phenyl lower alkyl group (of which the phenyl ring may be substituted by at least one group selected from the group consisting of a halogen atom, a halogen-substituted or unsubstituted lower alkyl group and a halogen-substituted or unsubstituted lower alkoxy group), a phenyl group (of which the phenyl ring may be substituted by at least one group selected from the group consisting of a halogen atom, a halogen-substituted or unsubstituted lower alkyl group and a halogen-substituted or unsubstituted lower alkoxy group) or a pyridyl group (of which the pyridine ring may be substituted by at least one halogen atom); $R^{1c}$ and $R^{2c}$ may be also taken together to form a piperidinyl group with an adjacent nitrogen atom with or without another heteroatom; the fourth position of the piperidinyl group may be substituted by at least 1 to 2 groups selected from the group consisting of a hydroxyl group, a phenoxy group (of which the phenyl ring may be substituted by at least one groups selected from the group consisting of a halogen atom, a halogen-substituted or unsubstituted lower alkyl group and a halogen-substituted or unsubstituted lower alkoxy group), a phenyl lower alkyl group (of which the phenyl ring may be substituted by at least one group selected from the group consisting of a halogen atom, a halogen-substituted or unsubstituted lower alkyl group and a halogen-substituted or unsubstituted lower alkoxy group), a phenyl group (of which the phenyl ring may be substituted by at least one group selected from the group consisting of a halogen atom, a halogen-substituted or unsubstituted lower alkyl group and a halogen-substituted or unsubstituted lower alkoxy group), a naphthyloxy group (of which the naphthalene ring may be substituted by at least one lower alkyl group) and a pyridyloxy group; or $R^{1c}$ and $R^{2c}$ may be also taken together to form a piperazinyl group with an adjacent nitrogen atom with or without another heteroatom; the fourth position of the piperazinyl group may be substituted by one group selected from the group consisting of a lower alkyl group, a phenyl lower alkyl group (of which the phenyl ring may be substituted by at least one group selected from the group consisting of a halogen atom, a halogen-substituted or unsubstituted lower alkyl group and a halogen-substituted or unsubstituted lower alkoxy group), a naphthyl-substituted lower alkyl group, a pyridyl-substituted lower alkyl group (of which the pyridine ring may be substituted by at least one halogen atom), a furyl-substituted lower alkyl group, a thienyl-substituted lower alkyl group (of which the thiophene ring may be substituted by at least one halogen atom), a thiazolyl-substituted lower alkyl group (of which the thiazole ring may be substituted by at least one lower alkyl group), an isooxazolyl-substituted C1-6 alkyl group (of which the isooxazole ring may be substituted by at least one lower alkyl group) and a phenyl group (of which the phenyl ring may be substituted by at least one group selected from the group consisting of a halogen atom, a halogen-substituted or unsubstituted lower alkyl group and a halogen-substituted or unsubstituted lower alkoxy group).

According to the Reaction scheme-4, the compound of the formula (9) is produced by allowing a compound represented by the formula (7) to react with a compound represented by the formula (1a) or a salt thereof in the presence or absence of a basic compound to give a compound represented by the formula (8), and then by cyclization of the obtained compound represented by the formula (8) in the presence of a basic compound.

As for the proportion of the compound (1a) and the compound (7), the proportion of the latter to the former is usually 0.5 to 5-fold mole, preferably 0.5 to 2-fold mole.

The reaction of the compound (7) and the compound (1a) is conducted in the presence or absence of an acidic compound or a basic compound in an appropriate solvent or without a solvent.

Examples of the acidic compound include solid acids and Lewis acids. Specific Examples of the solid acids include silica gel and zeolite. Examples of the Lewis acids include metal triflates such as scandium triflate and yttrium triflate, boron trifluoride-ether complex and titanium tetrachloride.

As the basic compound, a wide variety of known inorganic basic compounds and organic basic compounds can be used.

Examples of the inorganic basic compounds include metal hydrides, hydroxides, carbonates, hydrogen carbonates, phosphates and metal fluorides.

Specific Examples of the metal hydride include sodium hydride and potassium hydride. Specific Examples of the hydroxide include sodium hydroxide, cesium hydroxide and potassium hydroxide. Specific Examples of the carbonate include sodium carbonate, cesium carbonate and potassium carbonate. Specific Examples of the hydrogen carbonate include sodium hydrogen carbonate and potassium hydrogen carbonate. Specific examples of the phosphate include tripotassium phosphate, dipotassium hydrogen phosphate, trisodium phosphate and disodium hydrogen phosphate. Specific examples of the metal fluoride include sodium fluoride, potassium fluoride, cesium fluoride and a mixture of these with a carrier such as alumina.

In addition to those listed above, the inorganic basic compounds include sodium amide.

Examples of the organic basic compound include metal alcoholates and acetates. Specific examples of the metal alcoholate include sodium methoxide, sodium ethoxide, potassium tert-butoxide, sodium tert-butoxide, potassium tert-pentoxide and sodium tert-pentoxide. Specific examples of the acetate include sodium acetate and potassium acetate.

The basic compound is used alone or in a mixture of two or more kinds.

The amount of the basic compound is usually a catalytic amount, preferably 0.1 to 3 mole, more preferably 0.1 to 2 mole based on 1 mole of the compound of the formula (1a).

As the solvent, known solvents can be widely used as long as the reaction is not inhibited. Examples of such solvents include amides such as N,N-dimethylformamide (DMF), N,N-dimethylacetoamide and N-methyl pyrrolidone, aprotic polar solvents such as dimethylsulfoxide (DMSO) and acetonitrile, ketone solvents such as acetone and methyl ethyl ketone, hydrocarbon solvents such as benzene, toluene, xylene, tetralin and liquid paraffin, alcohol solvents such as methanol, ethanol, isopropanol, n-butanol and tert-butanol, ether solvents such as tetrahydrofuran (THF), dioxane, dipropylether, diethylether, monoglyme and diglyme, ester solvents such as ethyl acetate, methyl acetate, propyl acetate, n-butyl acetate, tert-butyl acetate, pentyl acetate, methyl propionate, ethyl propionate, propyl propionate, n-butyl propionate and tert-butyl propionate and a mixed solvent of these. These solvents may contain water.

Instead of using the compound (1a) and the basic compound, a salt of the compound (1a) may be used. Examples of such salt include alkali metal salts of the compound (1a), such as a sodium salt and a potassium salt.

The reaction of the compound of the formula (7) and the compound of the formula (1a) is conducted usually at room temperature to 150° C., preferably at room temperature to 120° C. The reaction time is usually 10 minutes to 48 hours, preferably 10 minutes to 24 hours, more preferably 10 minutes to 10 hours.

The compound represented by the formula (9) according to the present invention is produced by subjecting the compound represented by the formula (8) to cyclization reaction. The cyclization reaction is carried out, for example, by dissolving the compound represented by the formula (8) obtained above in a reaction solvent, adding a basic compound thereto and stirring the mixture at a pre-determined temperature.

As the reaction solvent and the basic compound, the same reaction solvents and basic compounds used in the reaction of the compound of the formula (7) and the compound of the formula (1a) can be used.

The amount of the basic compound is usually equimolar to excess mole, preferably equimolar to 5 mole, more preferably equimolar to 2 mole based on 1 mole of the compound of the formula (8).

The reaction temperature of the cyclization reaction is usually −20 to 150° C., preferably −10 to 120° C., more preferably −10 to 100° C. The reaction time is usually 10 minutes to 48 hours, preferably 10 minutes to 24 hours, more preferably 20 minutes to 4 hours.

In the present invention, a reaction mixture can be subjected to the subsequent cyclization without isolating a compound of the formula (8) produced by the reaction of the compound of the formula (7) and the compound of the formula (1a), whereby the objective compound represented by the formula (9) can be produced.

When the reaction is conducted by using a basic compound in an equimolar to an excess molar amount based on 1 mole of the compound (1a) at 50 to 100° C., a compound of the formula (9) can be produced at once without isolation of the intermediate (8). The same applies in the case of using an alkali metal salt (e.g., sodium salt, potassium salt) of the compound (1a).

The compounds represented by the formula (1) (final products) and the intermediates obtained by the above-mentioned Reaction formulas in the present invention include stereoisomers and optical isomers.

The compounds according to the present invention include pharmaceutically acceptable salts thereof. Examples of such salt include inorganic acid salts such as hydrochloride, hydrobromate, nitrate, sulfate and phosphate, and organic acid salts such as methanesulfonate, p-toluenesulfonate, acetate, citrate, tartarate, maleate, fumarate, malate and lactate.

The objective compounds obtained by the method of the present invention can be isolated from the reaction system by a usual isolation process and can be further purified. As the process of isolation and purification, for example, distillation, recrystallization, column chromatography, ion exchange chromatography, gel chromatography, affinity chromatography, preparative thin layer chromatography and solvent extraction can be adopted.

According to the method of the present invention, the objective aminophenol compound of the formula (1) can be produced at a high yield and a high purity without using expensive catalysts such as bases and metals and in addition, only by one step without any complicated steps.

Accordingly, the method of the present invention is extremely advantageous industrially.

EXAMPLES

In the following, the present invention is revealed in more detail referring to Examples.

Reference Example 1

Production of
1-t-butoxycarbonyl-4-mesyloxypiperidine

To 300 ml of an ethyl acetate solution containing 30.00 g of N-t-butoxycarbonyl-4-hydroxypiperidine and 41.6 ml of triethylamine was added dropwise 17.3 ml of mesyl chloride at −10° C. over 10 minutes. The temperature increased to 5° C. due to heat generation. After stirring with cooling in an ice bath for 10 minutes, 90 ml of water was carefully added dropwise to the reaction mixture. The temperature increased from 0° C. to 6° C. due to heat generation. After stirring for 10 minutes, the mixture was separated and the organic phase washed with water (90 ml×2), saturated saline (90 ml), water (90 ml) and saturated saline (90 ml) in this order. After drying with anhydrous magnesium sulfate, concentration was conducted under reduced pressure and 40.74 g of 1-t-butoxycarbonyl-4-mesyloxypiperidine was obtained.

$^1$H-NMR (300 MHz, CDCl$_3$) δppm: 1.46 (9H, s), 1.48-1.90 (2H, m), 1.90-2.04 (2H, m), 3.04 (3H, s), 3.32-3.40 (2H, m), 3.61-3.81 (2H, m), 4.88 (1H, ddd, J=11.5 Hz, J=7.7 Hz, J=3.7 Hz).

Reference Example 2

Production of
4-(4-trifluoromethoxyphenoxy)piperidine 40.74 g of 1-t-butoxycarbonyl-4-mesyloxypiperidine obtained in the above Reference Example 1, 14.43 g of 4-trifluoromethoxyphenol and 4.50 g of tetra-n-butyl ammonium chloride were suspended in 72 ml of water. Next, after adding 33.59 g of potassium carbonate to the suspension, the suspension was subjected to reflux for 8 hours (inner temperature: 101° C.). After leaving the suspension at room temperature overnight, 216 ml of n-hexane was added thereto and stirring was conducted for 5 minutes. Thereto was added 72 ml of 10% aqueous sodium hydroxide solution and after stirring, the mixture was separated. After washing with water (72 ml×2), the organic phase was dried over anhydrous magnesium sulfate and concentrated under reduced pressure, and 39.02 g of a mixture of 1-t-butoxycarbonyl-4-(4-trifluoromethoxyphenoxy)piperidine and 1-t-butoxycarbonyl-3,4-dehydropiperidine was obtained.

From $^1$H-NMR (CDCl$_3$) analysis, the mixture was regarded to contain 28.48 g of 1-t-butoxycarbonyl-4-(4-trifluoromethoxyphenoxy)piperidine and 10.54 g of 1-t-butoxy-3,4-dehydropiperidine.

The above mixture was dissolved in 117 ml of ethyl acetate, and 51 ml of 4N-hydrochloric acid-ethyl acetate solution was added thereto dropwise at room temperature over 10 minutes. After stirring the mixture at the room temperature for an hour, thin layer chromatography analysis revealed that the raw materials were not completely consumed, and so further 51 ml of 4N-hydrochloric acid-ethyl acetate solution was added thereto. The mixture was further stirred at room temperature for 3 hours and left overnight at the room temperature. The reaction solution was cooled with ice and 163 ml of 10% aqueous sodium hydroxide solution was carefully poured thereto. The temperature increased to 23° C. due to heat generation. The mixture was separated and the ethyl acetate phase washed with saturated saline (80 ml) and water (80 ml), and then dried over anhydrous magnesium sulfate. The solvent was concentrated under reduced pressure and 19.45 g of pale yellow solid of 4-(4-trifluoromethoxyphenoxy)piperidine was obtained.

$^1$H-NMR (300 MHz, CDCl$_3$) δppm: 1.54 (1H, br. s), 1.58-1.73 (2H, m), 1.94-2.06 (2H, m), 2.72 (2H, ddd, J=12.5 Hz, J=9.4 Hz, J=3.1 Hz), 3.14 (2H, ddd, J=12.5 Hz, J=4.8 Hz, J=4.8 Hz), 4.33 (1H, ddd, J=12.3 Hz, J=8.4 Hz, J=4.0 Hz), 6.89 (2H, d, J=9.1 Hz), 7.12 (2H, d, J=9.1 Hz).

Reference Data 1-t-butoxycarbonyl-4-(4-trifluoromethoxyphenoxy)piperidine $^1$H-NMR (300 MHz, CDCl$_3$) δppm: 1.47 (9H, s), 1.68-1.82 (2H, m), 1.82-2.00 (2H, m), 3.29-3.40 (2H, m), 3.63-3.78 (2H, m), 4.39-4.49 (1H, m), 6.90 (2H, d, J=8.6 Hz), 7.13 (2H, d, J=8.6 Hz).

1-t-butoxycarbonyl-3,4-dehydropiperidine $^1$H-NMR (300 MHz, CDCl$_3$) δppm: 1.46 (9H, s), 2.13 (2H, br.s), 3.49 (2H, t, J=5.7 Hz), 3.88 (2H, br, t, J=2.5 Hz), 5.58-5.74 (1H, m), 5.74-5.91 (1H, m).

Reference Example 3

Production of (2R)-2-methyl-6-nitro-2-{4-[4-(4-trifluoromethoxyphenoxy)piperidine-1-yl]phenoxymethyl}-2,3-dihydroimidazo[2,1-b]oxazole 1-(4-hydroxyphenyl)-4-(4-trifluoromethoxyphenoxy)piperidine (2034 g) and 2-chloro-1-[(2R)-2-methyl-2,3-epoxypropyl]-4-nitroimidazole (1388 g) were heated with stirring for 8 hours at about 100° C. and crude 1-{4-[(2R)-3-(2-chloro-4-nitroimidazole-1-yl)-2-hydroxy-2-methylpropoxy]phenyl}-4-(4-trifluoromethoxyphenoxy)piperidine was obtained. At the point where this was cooled to 88° C., dimethylformamide (2.5 L) was added and dissolved therein. After leaving the mixture at room temperature for 13 hours, dimethylformamide (15.8 L) was further added and the mixture was cooled to −9° C. Sodium tert-butoxide (715 g) was gradually added thereto at not more than 0° C. over 3.5 hours. After stirring for further 15 minutes, the reaction mixture was poured into a mixture of water (41.2 L) and ethyl acetate (2.1 L) at room temperature. After stirring for an hour at 30° C., the precipitate was filtrated. Crystals were washed with water (9.2 L) and then with ethyl acetate (8.2 L) under reflux. Upon cooling to 5° C., the precipitate was filtrated. The precipitate washed with ethyl acetate (2.2 L), and dried by air blasting at 60° C. for 18 hours to obtain (2R)-2-methyl-6-nitro-2-{4-[4-(4-trifluoromethoxyphenoxy)piperidine-1-yl]phenoxymethyl}-2,3-dihydroimidazo[2,1-b]oxazole (1548 g; yield 50%).

$^1$H-NMR (300 MHz, CDCl$_3$) δppm: 1.76 (3H, s), 1.88-2.04 (2H, m), 2.04-2.21 (2H, m), 2.93-3.08 (2H, m), 3.30-3.45 (2H, m), 4.03 (1H, d, J=10.2 Hz), 4.04 (1H, d, J=10.2 Hz), 4.18 (1H, d, J=10.2 Hz), 4.35-4.47 (1H, m), 4.50 (1H, d, J=10.2 Hz), 6.78 (2H, d, J=8.6 Hz), 6.86-6.97 (4H, m), 7.14 (2H, d, J=8.6 Hz), 7.55 (1H, s).

The NMR spectrum data of 1-{4-[(2R)-3-(2-chloro-4-nitroimidazole-1-yl)-2-hydroxy-2-methylpropoxy]phenyl}-4-(4-trifluoromethoxyphenoxy)piperidine is as follows.

$^1$H-NMR (300 MHz, CDCl$_3$) δppm: 1.33 (3H, s), 1.88-2.02 (2H, m), 2.03-2.19 (2H, m), 2.95-3.08 (2H, m), 3.30-3.44 (2H, m), 3.81 (1H, d, J=9.4 Hz), 3.85 (1H, d, J=9.4 Hz), 4.15 (1H, d, J=14.3 Hz), 4.28 (1H, d, J=14.3 Hz), 4.37-4.48 (1H, m), 6.81 (2H, d, J=8.6 Hz), 6.87-6.97 (4H, m), 7.14 (2H, d, J=8.6 Hz), 8.01 (1H, s).

Example 1

Production of 1-(4-hydroxyphenyl)-4-(4-trifluoromethoxyphenoxy)piperidine (1) 261 mg of 4-(4-trifluoromethoxyphenoxy)piperidine and 224 mg of 1,4-cyclohexanedione were heated under reflux in 5 ml of ethanol and reacted for 7 hours. After concentrating the reaction mixture under reduced pressure, the resultant was separated by silica gel column chromatography (n-hexane:ethyl acetate=3:1) and 154.9 mg of 1-(4-hydroxyphenyl)-4-(4-trifluoromethoxyphenoxy)piperidine was obtained (yield 43.8%).

$^1$H-NMR (300 MHz, CDCl$_3$) δppm: 1.91-2.01 (2H, m), 2.07-2.15 (2H, m), 2.94-3.02 (m, 2H), 3.32-3.39 (2H, m), 4.37-4.45 (1H, m), 4.7 (1H, br), 6.74-6.79 (2H, m), 6.87-6.94 (4H, m), 7.11-7.17 (2H, m).

(2) 261 mg of 4-(4-trifluoromethoxyphenoxy)piperidine, 224 mg of 1,4-cyclohexanedione and 4 mg of 10% palladium-carbon were heated in ethanol and reacted at 70° C. to 80° C. for 9 hours. After the completion of the reaction, the resultant was separated by silica gel column chromatography (n-hexane:ethyl acetate=3:1) and 315 mg of 1-(4-hydroxyphenyl)-4-(4-trifluoromethoxyphenoxy)piperidine was obtained (yield 89%).

$^1$H-NMR (300 MHz, CDCl$_3$) δppm: 1.91-2.01 (2H, m), 2.07-2.15 (2H, m), 2.94-3.02 (m, 2H), 3.32-3.39 (2H, m), 4.37-4.45 (1H, m), 4.7 (1H, br), 6.74-6.79 (2H, m), 6.87-6.94 (4H, m), 7.11-7.17 (2H, m).

(3) 100 mg of 4-(4-trifluoromethoxyphenoxy)piperidine, 64 mg of 1,4-cyclohexanedione and 0.02 ml of triethylamine were heated in 15 ml of ethanol and reacted at 50° C. to 60° C. for 6 hours. After the completion of the reaction, the reaction mixture was concentrated under reduced pressure and ethyl acetate was added thereto to prepare an ethyl acetate solution, to which p-toluenesulfonic acid was added. After leaving at room temperature for 30 minutes, the precipitate was filtrated and washed with ethyl acetate. The obtained crystal was air-dried and 139 mg of 1-(4-hydroxyphenyl)-4-(4-trifluoromethoxyphenoxy)piperidine p-toluenesulfonate was obtained.

m.p.: 218.9-219.6° C.

$^1$H-NMR (300 MHz, DMSO-d$_6$) δppm: 1.9-2.2 (2H, br), 2.27 (3H, s), 2.2-2.4 (2H, br), 3.62 (2H, br), 4.77 (1H, br), 6.90 (2H, d, J=8.9 Hz), 7.11 (2H, d, J=7.8 Hz), 7.1-7.2 (2H, m), 7.32 (2H, d, J=8.9 Hz), 7.45-7.55 (2H, m), 7.49 (2H, d, J=7.9 Hz).

(4) 4.00 g of 4-(4-trifluoromethoxyphenoxy)piperidine, 2.575 g of 1,4-cyclohexanedione and 2.16 ml of triethylamine were heated in 60 ml of ethanol and reacted at 50° C. to 60° C. for 6 hours. After the completion of the reaction, the reaction mixture was concentrated under reduced pressure and ethyl acetate was added thereto to prepare an ethyl acetate solution, to which 4.37 g of p-toluenesulfonic acid monohydrate was added. After leaving at room temperature for 30 minutes, the precipitate was filtrated, washed with ethyl acetate and air-dried, and 5.116 g of 1-(4-hydroxyphenyl)-4-(4-trifluoromethoxyphenoxy)piperidine p-toluenesulfonate was obtained (yield 63.75%).

m.p.: 218.9-219.6° C.

$^1$H-NMR (300 MHz, DMSO-d$_6$) δppm: 1.9-2.2 (2H, br), 2.27 (3H, s), 2.2-2.4 (2H, br), 3.62 (2H, br), 4.77 (1H, br), 6.90 (2H, d, J, 8.9 Hz), 7.11 (2H, d, J=7.8 Hz), 7.1-7.2 (2H, m), 7.32 (2H, d, J=8.9 Hz), 7.45-7.55 (2H, m), 7.49 (2H, d, J=7.9 Hz).

(5) 1.00 g of 1-(4-hydroxyphenyl)-4-(4-trifluoromethoxyphenoxy)piperidine p-toluenesulfonate was recrystallized in a mixture of 4.2 ml of ethanol and 2.8 ml of water. The precipitate was filtrated and washed with 60% ethanol. The obtained crystal was air-dried and 0.7636 g of 1-(4-hydroxyphenyl)-4-(4-trifluoromethoxyphenoxy)piperidine p-toluenesulfonate was obtained (yield 76.3%)

m.p.: 218.9-219.6° C.

$^1$H-NMR (300 MHz, DMSO-d$_6$) δppm: 1.9-2.2 (2H, br), 2.27 (3H, s), 2.2-2.4 (2H, br), 3.62 (2H, br), 4.77 (1H, br), 6.90 (2H, d, J=8.9 Hz), 7.11 (2H, d, J=7.8 Hz), 7.1-7.2 (2H, m), 7.32 (2H, d, J=8.9 Hz), 7.45-7.55 (2H, m) 7.49 (2H, d, J=7.9 Hz).

Example 2

Production of 1-(4-hydroxyphenyl)-4-hydroxypiperidine 202 mg of 4-hydroxypiperidine and 448 mg of 1,4-cyclohexanedione were heated under reflux in 10 ml of ethanol and reacted for 9 hours with introducing air with a pump. During the reaction, ethanol was added as needed. After the completion of the reaction, the resultant was separated by silica gel column chromatography (n-hexane:ethyl acetate=2:1) and 0.218 g of 1-(4-hydroxyphenyl)-4-hydroxypiperidine was obtained (yield 56.48%).

$^1$H-NMR (300 MHz, CDCl$_3$) δppm: 1.66-1.78 (2H, m), 1.98-2.05 (2H, m), 2.77-2.86 (2H, m), 3.35-3.42 (2H, m), 3.78-3.85 (1H, m), 4.5 (1H, br), 6.73-6.78 (2H, m), 6.84-6.90 (2H, m).

Example 3

Production of 1-(4-hydroxyphenyl)piperidine 0.85 g of piperidine and 2.24 g of 1,4-cyclohexanedione were heated with stirring in 15 ml of ethanol at 50 to 60° C. and reacted in air for 8 hours. During the reaction, ethanol was added as needed. After the completion of the reaction, the reaction mixture was concentrated under reduced pressure and the resultant was separated by silica gel column chromatography (n-hexane:ethyl acetate=2:1) and 0.95 g of 1-(4-hydroxyphenyl)piperidine was obtained (yield 53.7%).

$^1$H-NMR (300 MHz, CDCl$_3$) δppm: 1.45-1.58 (2H, m), 1.68-1.76 (4H, m), 3.01 (4H, t-like, J=5.3 Hz, J=5.4 Hz), 6.74 (2H, d, J=8.9 Hz), 6.87 (2H, d, J=8.9 Hz).

Example 4

Production of 1-(4-hydroxyphenyl)piperidine 0.85 g of piperidine, 1.68 g of 1,4-cyclohexanedione and 40 mg of 10% palladium-carbon were heated with stirring in 40 ml of ethanol at 50° C. to 60° C. and reacted for 8 hours under air bubbling. During the reaction, ethanol was added as needed. After the completion of the reaction, the catalyst was removed by filtration and the filtrate was concentrated under reduced pressure. The resultant was purified by silica gel column chromatography (n-hexane:ethyl acetate=4:1) and purified by silica gel column chromatography again, and 0.668 g of 1-(4-hydroxyphenyl)piperidine was obtained (yield 43.4%).

$^1$H-NMR (300 MHz, CDCl$_3$) δppm: 1.50-1.58 (2H, m), 1.67-1.76 (4H, m), 3.01 (4H, t-like, J=5.3 Hz, J=5.6 Hz), 6.74 (2H, d, J=9.0 Hz), 6.87 (2H, d, J=9.0 Hz).

Example 5

Production of 1-(4-hydroxyphenyl)-4-methylpiperadine 1.00 g of 1-methylpiperadine and 2.24 g of 1,4-cyclohexanedione were heated with stirring in 15 ml of ethanol at 50° C. to 60° C. and reacted in air for 8 hours. During the reaction, ethanol was added as needed. After the completion of the reaction, the reaction mixture was concentrated under reduced pressure and the resultant was purified by silica gel column chromatography (ethyl acetate:methanol=3:1) and 0.65 g of 1-(4-hydroxyphenyl)-4-methylpiperadine was obtained (yield 33.9%).

$^1$H-NMR (300 MHz, CDCl$_3$) δppm: 2.37 (3H, s), 2.63 (4H, t-like, J=5.1 Hz, J=4.9 Hz), 3.10 (4H, t-like, J=5.1 Hz, J=4.9 Hz), 6.74 (2H, d, J=8.9 Hz), 6.84 (2H, d, J=9.0 Hz).

Example 6

Production of 1-(4-hydroxyphenyl)-4-methylpiperadine 1.00 g of 1-methylpiperadine, 1.68 g of 1,4-cyclohexanedione and 40 mg of 10% palladium-carbon were heated with stirring in 40 ml of ethanol at 50° C. to 60° C. and reacted for 8 hours under air bubbling. During the reaction, ethanol was added as needed. After the completion of the reaction, the catalyst was removed by filtration and the filtrate was concentrated under reduced pressure. The resultant was purified by silica gel column chromatography (ethyl acetate:methanol=3:1) and 1.26 g of 1-(4-hydroxyphenyl)-4-methylpiperadine was obtained (yield 65.5%).

$^1$H-NMR (300 MHz, CDCl$_3$) δppm: 2.37 (3H, s), 2.64 (4H, t-like, J=5.1 Hz, J=4.8 Hz), 3.10 (4H, t-like, J=5.1 Hz, J=4.9 Hz), 6.78 (2H, d, J=9.0 Hz), 6.84 (2H, d, J=9.0 Hz).

Example 7

Production of N-(4-hydroxyphenyl)-N-methylaniline 1.07 g of N-methylaniline, 2.24 g of 1,4-cyclohexanedione and 1.4 ml of triethylamine were heated with stirring in 15 ml of ethanol at 50° C. to 60° C. and reacted in air for 8 hours. During the reaction, ethanol was added as needed. After the completion of the reaction, the reaction mixture was concentrated under reduced pressure and the resultant was separated by silica gel column chromatography (n-hexane:ethyl acetate=3:1) and 0.64 g of N-(4-hydroxyphenyl)-N-methylaniline was obtained (yield 32.1%).

$^1$H-NMR (300 MHz, CDCl$_3$) δppm: 3.25 (3H, s), 5.1 (1H, br), 6.76-6.85 (3H, m), 6.83 (2H, d, J=8.9 Hz), 7.04 (2H, d, J=8.9 Hz), 7.16-7.23 (2H, m).

Example 8

Production of N-(4-hydroxyphenyl)aniline 0.93 g of aniline, 2.24 g of 1,4-cyclohexanedione and 1.4 ml of triethylamine were heated with stirring in 15 ml of ethanol at 50° C. to 60° C. and reacted in air for 8 hours. During the reaction, ethanol was added as needed. After concentrating the reaction mixture under reduced pressure, the resultant was purified by silica gel column chromatography (n-hexane:ethyl acetate=3:1) and 0.50 g of N-(4-hydroxyphenyl)aniline was obtained (yield 27.4%).

$^1$H-NMR (300 MHz, CDCl$_3$) δppm: 4.70 (1H, br), 5.48 (1H, br), 6.76-6.87 (1H, m), 6.79 (2H, d, J=9.0 Hz), 6.88-6.92 (2H, m), 7.00-7.06 (1H, m), 7.03 (2H, d, J=8.7 Hz), 7.18-7.28 (3H, m).

Example 9

Production of N-(4-hydroxyphenyl)dibenzylamine 1.97 g of dibenzylamine, 1.68 g of 1,4-cyclohexanedione and 40 mg of 10% palladium-carbon were heated with stirring in 40 ml of ethanol at 50° C. to 60° C. and reacted for 8 hours under air bubbling. During the reaction, ethanol was added as needed. After the completion of the reaction, the catalyst was removed by filtration and the filtrate was concentrated under reduced pressure. The resultant was purified by silica gel column chromatography (n-hexane:ethyl acetate=30:1) and further separated by silica gel column chromatography (n-hexane:ethyl acetate=10:1), and 1.67 g of N-(4-hydroxyphenyl)dibenzylamine was obtained (yield 57%).

$^1$H-NMR (300 MHz, CDCl$_3$) δppm: 1.5-2.5 (1H, br), 3.83 (4H, s), 6.84-6.90 (10H, m).

Example 10

Production of 1-(4-hydroxyphenyl)-4-(4-trifluoromethoxyphenoxy)piperidine

A suspension in 4 ml of 90% ethanol containing 100 mg of 4-(4-trifluoromethoxyphenoxy)piperidine, 86 mg of 1,4-cyclohexanedione and 100 mg of 5% palladium-carbon (containing 54% of water) was stirred under argon stream at 70 to 80° C. for 10 hours. After cooling the reaction mixture to room temperature, the catalyst was removed by filtration. To the mother liquor was added 201 mg of p-toluenesulfonic acid monohydrate and the mixture was concentrated under reduced pressure. 8 ml of ethyl acetate was added to the residue and the mixture was concentrated under reduced pressure. 8 ml of ethyl acetate was further added to the residue and washing by dispersing was conducted at 70° C. After ice-cooling, the precipitated crystal was filtrated, vacuum-dried at room temperature and 123 mg of 1-(4-hydroxyphenyl)-4-(4-trifluoromethoxyphenoxy)piperidine p-toluenesulfonate was obtained (yield 61.2%).

m.p.: 218.9-219.6° C.

$^1$H-NMR (300 MHz, DMSO-d$_6$) δppm: 1.9-2.2 (2H, br), 2.27 (3H, s), 2.2-2.4 (2H, br), 3.62 (2H, br), 4.77 (1H, br), 6.90 (2H, d, J=8.9 Hz), 7.11 (2H, d, J=7.8 Hz), 7.1-7.2 (2H, m), 7.32 (2H, d, J=8.9 Hz), 7.45-7.55 (2H, m), 7.49 (2H, d, J=7.9 Hz).

The invention claimed is:

1. A method of producing an aminophenol compound represented by the formula (1)

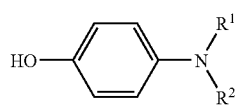

(1)

wherein R$^1$ and R$^2$, taken together with the adjacent nitrogen atom, form a 5- or 6-membered heterocyclic group selected from the group consisting of a piperidinyl and a piperazinyl group and the heterocyclic group may be substituted by 1 to 3 substituents selected from the group consisting of a hydroxyl group; a lower alkyl group which may have 1 to 3 substituents selected from the group consisting of a halogen atom, a hydroxyl group, and an aryl group; an aryl group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms; and an aryloxy group which may have 1 to 3 substituents selected from the group consisting of a lower alkyl group which may have 1 to 3 substituents selected from the group consisting of a halogen atom and a hydroxyl group, a lower alkoxy group which may have 1 to 3 substituents selected from the group consisting of a halogen atom and a hydroxyl group, and halogen atoms, which comprises allowing a cyclohexanedione compound represented by the formula (2)

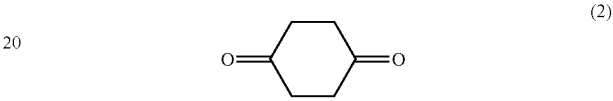

(2)

to react with an amine compound represented by the formula (3)

(3)

(wherein R$^1$ and R$^2$ are as defined above), under a neutral or basic condition.

2. The method according to claim 1, wherein the aryl group is a phenyl group or a naphthyl group; and the aryloxy group is a phenoxy group or a naphthyloxy group.

3. The method according to claim 1, wherein the aminophenol compound is 1-(4-hydroxyphenyl)-4-(4-trifluoromethoxyphenoxy) piperidine, -(4-hydroxyphenyl)-4-hydroxypiperidine, 1-(4-hydroxyphenyl)piperidine, 1-(4-hydroxyphenyl)-4-methyl piperazine, N-(4-hydroxyphenyl)-N-methylaniline N-(4-hydroxyphenyl)aniline or N-(4-hydroxyphenyl)dibenzylamine.

4. The method according to claim 1, which, is conducted in the presence of a dehydrogenating agent, wherein the dehydrogenating agent is used in an amount of at least 1% by weight based on an amount of the amine compound of the formula (3).

5. The method according to claim 1, which is conducted without a dehydrogenating agent.

6. The method according to claim 1, which, is conducted under a neutral condition.

7. The method according to claim 1, which, is conducted in the presence of a basic compound, wherein the basic compound is used in an amount of 0.5 to 5 mole based on 1 mole of the amine compound of the formula (3).

8. The method according to claim 1, wherein the reaction is conducted at a reaction temperature of room temperature to 150° C.

9. The method according to claim 1, wherein the cyclohexanedione compound of the formula (2) is used in an equimolar amount to 10 mole based on 1 mole of the amine compound of the formula (3).

* * * * *

UNITED STATES PATENT AND TRADEMARK OFFICE
CERTIFICATE OF CORRECTION

| | | |
|---|---|---|
| PATENT NO. | : 7,750,156 B2 | Page 1 of 1 |
| APPLICATION NO. | : 10/593968 | |
| DATED | : July 6, 2010 | |
| INVENTOR(S) | : Hiroshi Kiyokawa | |

It is certified that error appears in the above-identified patent and that said Letters Patent is hereby corrected as shown below:

* In claim 3, column 24, lines 41-42, "-(4-hydroxyphenyl)-4-hydroxypiperidine," should read --1-(4-hydroxyphenyl)-4-hydroxypiperidine,--.

* In claim 3, column 24, lines 42-43, "1-(4-hydroxyphenyl)-4-methyl piperazine," should read --1-(4-hydroxyphenyl)-4-methylpiperazine,--.

In claim 4, column 24, line 46, "which, is conducted" should read --which is conducted--.

In claim 6, column 24, line 53, "which, is conducted" should read --which is conducted--.

In claim 7, column 24, line 55, "which, is conducted" should read --which is conducted--.

Signed and Sealed this
Twenty-third Day of August, 2011

David J. Kappos
*Director of the United States Patent and Trademark Office*